US00PP09076P

United States Patent [19]

Machin

[11] Patent Number: Plant 9,076

[45] Date of Patent: Mar. 14, 1995

[54] CHRYSANTHEMUM PLANT NAMED ROYALIST

[75] Inventor: Barrie J. Machin, Hants, England

[73] Assignee: Goldstock Breeding Limited, Fareham, England

[21] Appl. No.: 181,106

[22] Filed: Jan. 13, 1994

[51] Int. Cl.[6] ..... A01H 5/00

[52] U.S. Cl. ..... Plt./80

[58] Field of Search ..... Plt. 80, 81

*Primary Examiner*—Howard J. Locker

*Attorney, Agent, or Firm*—Foley & Lardner

[57] ABSTRACT

A new Chrysanthemum cultivar named Royalist characterized by the combined features of decorative capitulum type, incurving inner ray florets and reflexing outer ray florets, pink ray floret color, 80–90 mm capitulum diameter, 56–63 days flowering response period, plant height of 91–102 cm when grown with 14 long days prior to start of short days, and its columnar spray formation.

3 Drawing Sheets

1

The present invention comprises a new and distinct cultivar of Chrysanthemum, botanically known as *Dendranthema grandiflora*, and referred to by the cultivar name Royalist.

Royalist was originated from a cross made by the inventor, Barrie J. Machin, in a controlled breeding program in Fareham, England in 1986.

The female parent of Royalist was an unpatented seedling known as Ballet which can be described as a cut spray mum cushion type having a plae pink ray floret color, a diameter of capitulum of 76 to 86 mm when fully open, a flowering response to short days of 61–63 days, a plant height of 86–96 cm when grown with 14 ong days prior to start of short days, a peduncle length of the first lateral of 8 to 15 cm and of the fourth lateral of 15–20 cm, and a terminal spray formation. The above characteristics are based on plants grown in Fareham, England.

The male parent of Royalist was an unpatented seedling identified as Bargain which can be described as a cut spray mum, cushion type having a pink ray floret color, diameter of capitulum of 90 mm when fully open, a flowering response to short days of 59–63 days, a plant height of 105–115 cm when grown with 14 long days prior to start of short days, a peduncle length of the first lateral of 12 cm and of the fourth lateral of 16 cm, and a cylindrical spray formation. The above characteristics are similarly based on plants grown in Fareham, England.

Royalist was discovered and selected as one flowering plant within the progeny of the stated cross by Barrie J. Machin in January 1987 in a controlled environment in Fareham, England.

The first act of asexual reproduction of Royalist was accomplished when vegetative cuttings were taken from the initial selection in October 1987 in a controlled environment in Fareham, England by Barrie J. Machin.

Horticultural examination of controlled flowerings of successive plantings has shown that the unique combination of characteristics as herein disclosed for Royalist are firmly fixed and are retained through successive generations of asexual reproduction.

Royalist has not been observed under all possible environmental conditions. The phenotype may vary somewhat with variations in environment such as temperature, light intensity and daylength, without, however, any variance in genotype.

2

The following observations, measurements and comparisons describe plants grown in Fareham, England under greenhouse conditions which approximate those generally used in commercial greenhouse practice.

The following traits have been repeatedly observed and are determined to be basic characteristics of Royalist, which, in combination, distinguish this Chrysanthemum as a new and distinct cultivar:

1. Decorative capitulum type.
2. Inner ray florets are incurving and outer ray florets are reflexing.
3. Pink ray floret color.
4. Diameter across face of capitulum of 80–90 mm when fully opened.
5. Flowering response under normal temperatures is 56 to 63 days after start of short days.
6. Plant height is 91 to 102 cm when grown with 14 long days prior to start of short days.
7. Peduncle length of the first lateral at flowering after removing the apical bud and without growth regulator applications is 7 cm; peduncle length of the fourth lateral at flowering is 10 cm.
8. Column spray formation.

The accompanying photographic drawings show typical inflorescence and leaf characteristics of Royalist, with the colors being as nearly true as possible with illustrations of this type.

Sheet 1 is a color photograph of Royalist grown as a single stem spray cut mum.

Sheet 2 is a black and white photograph showing the upper and under sides of the leaves of Royalist in three stages of development (mature, intermediate and immature).

Sheet 3 is a black and white photograph showing three views of the inflorescence of Royalist.

Of the commercial cultivars known to the inventor, the most similar in comparison to Royalist are the cultivars identified as Pink Gin, described in U.S. Plant Pat. No. 4,346, and Dark Pink Gin, described in U.S. Plant Pat. No. 4,997. Reference is made to attached Chart A, which compares certain characteristics of Royalist with the same characteristics of Pink Gin and Dark Pink Gin. With respect to Pink Gin, similar traits are capitulum diameter, decorative capitulum type, response, and spray formation. The ray floret color of both cultivars is described as pink, but Royalist is a slightly paler pink color than Pink Gin which can be described as a lavender pink. The ray floret color of Dark Pink Gin is an even darker lavender pink. The plant height of Royalist is considerably less than Pink Gin when the cultivars are grown under the same conditions. Further, substantially all of the ray florets on Pink Gin are incurving as contracted to Royalist in which the inner ray florets are incurving and at least a few of the outer ray florets are reflexing. Also, the inflorescence of Royalist has a greater depth at 2.5 cm than Pink Gin at approximately 2.0 cm.

In the following description, color references are made to The Royal Horticultural Society Colour Chart. The color values were determined on plant material grown as a single stem spray cut mum in Fareham, England in November 1987.

Classification:

*Botanical.*—*Dendranthema grandiflora* cv Royalist.

*Commercial.*—Decorative spray cut mum.

INFLORESCENCE

A. Capitulum:

*Form.*—Intermediate.

*Type.*—Decorative Depth: From bottom of flower at stem to top of fully open inflorescence is approximately 2.5 cm.

B. Cololla of ray florets:

*Color* (*general tonality from a distance of three meters*).—Pink.

*Color* (*upper surface*).—73B, fading to 73C as flowers mature.

*Color* (*under surface*).—73D.

*Shape.*—Inner petals are generally boat-shaped, that is, concave and longitudinally curved upwardly toward a blunt tip; outer petals are flatter, and extreme outer petals tend to reflex.

C. Corolla of disc florets:

*Color.*—Outer (mature) florets 11A. Inner (immature florets) 1B.

D. Reproductive organs:

*Androecium.*—Disc florets only; very small quantity of pollen.

*Gynoecium.*—Present on all ray florets.

PLANT

A. General appearance:

*Height.*—91–102 cm.

B. Foliage:

*Color* (*upper surface*).—146A.

*Color* (*under surface*).—146B.

*Shape.*—See photograph.

CHART A

Comparisons of plants grown as single system spray cut mums in Fareham, England

| CHARACTERISTICS | ROYALIST | PINK GIN | DARK PINK GIN |
|---|---|---|---|
| Ray Floret Color | | | |
| General | pink | Lavender pink | Dark lavender pink |
| Upper Surface | 73B | 75B | 75A |
| Under Surface | 73D | 75C | 75C |
| Capitula form and type | Intermediate | Incurving | Incurving |
| Diameter across face of capitula | 80–90 mm | 80–90 mm | 80–90 mm |
| Flowering response | 56–63 days | 56–63 days | 56–63 days |
| Plant height | 91–102 cm | 111–131 cm | 111–131 cm |
| Peduncle length | | | |
| First lateral | 7 cm | 7 cm | 7 cm |
| Fourth lateral | 10 cm | 10–11 cm | 10–11 cm |
| Spray formation | Columnar | Inverted pyramid | Inverted pyramid |

It is claimed:

1. A new and distinct Chrysanthemum plant named Royalist, as described and illustrated.

* * * * *

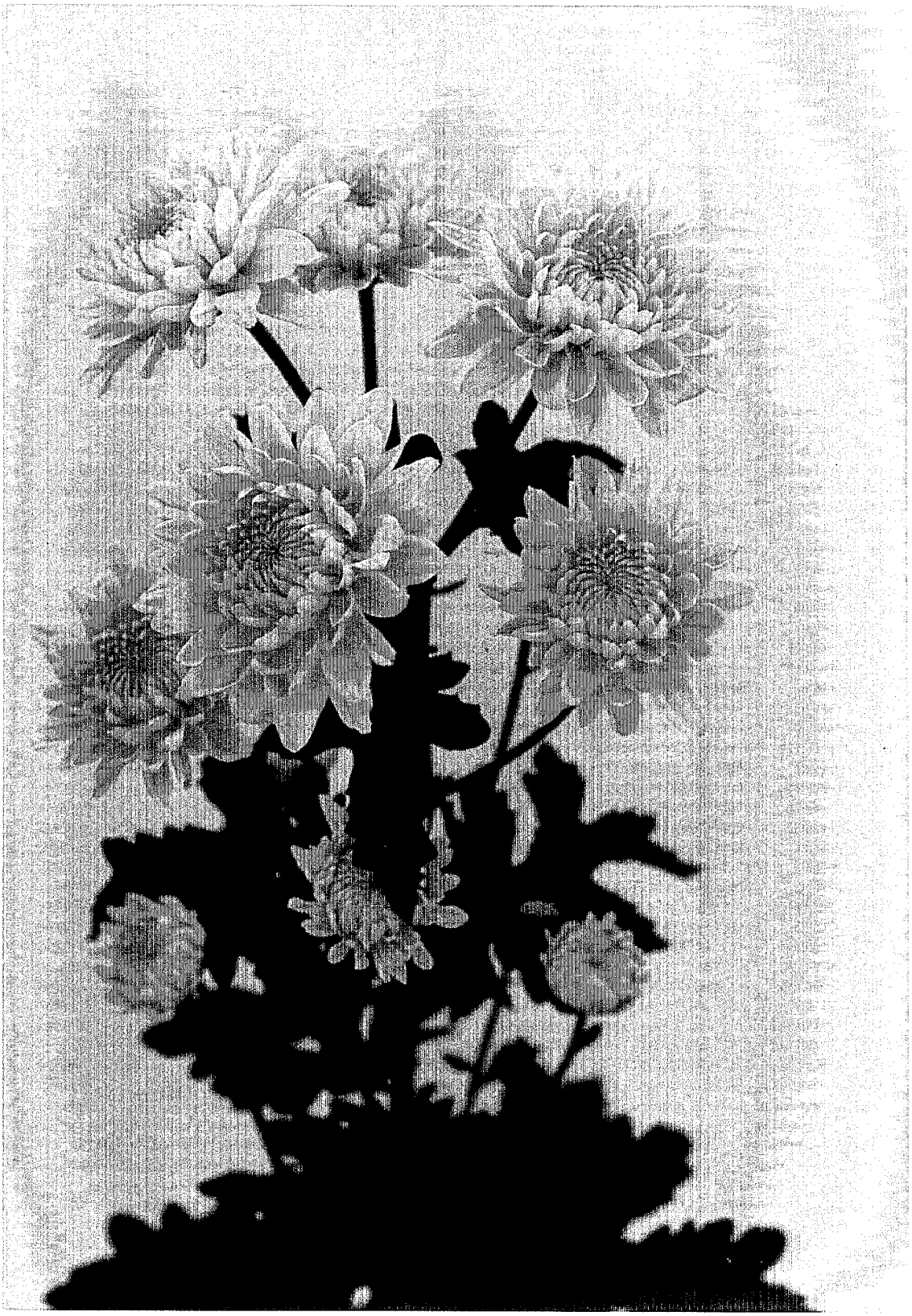

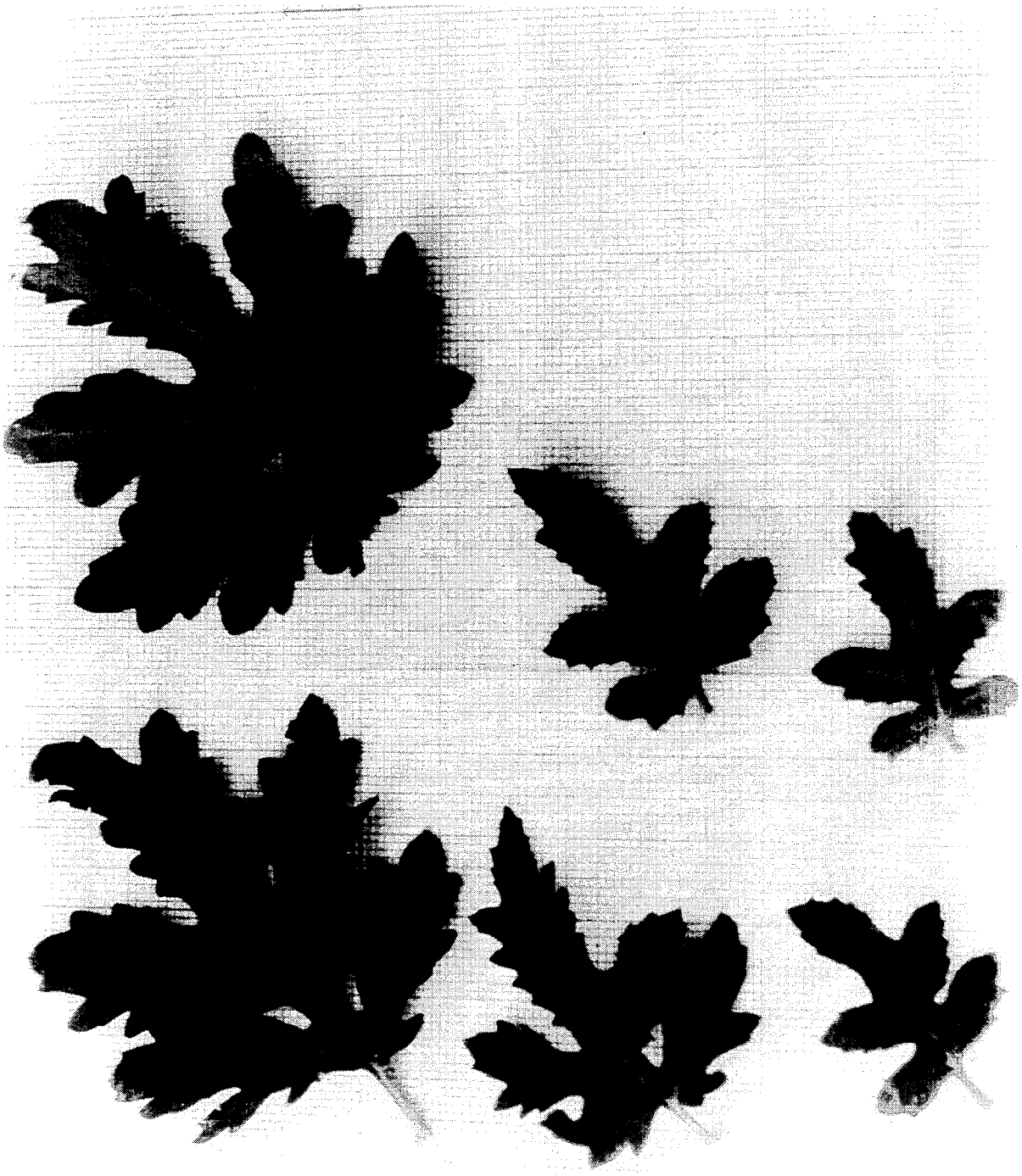

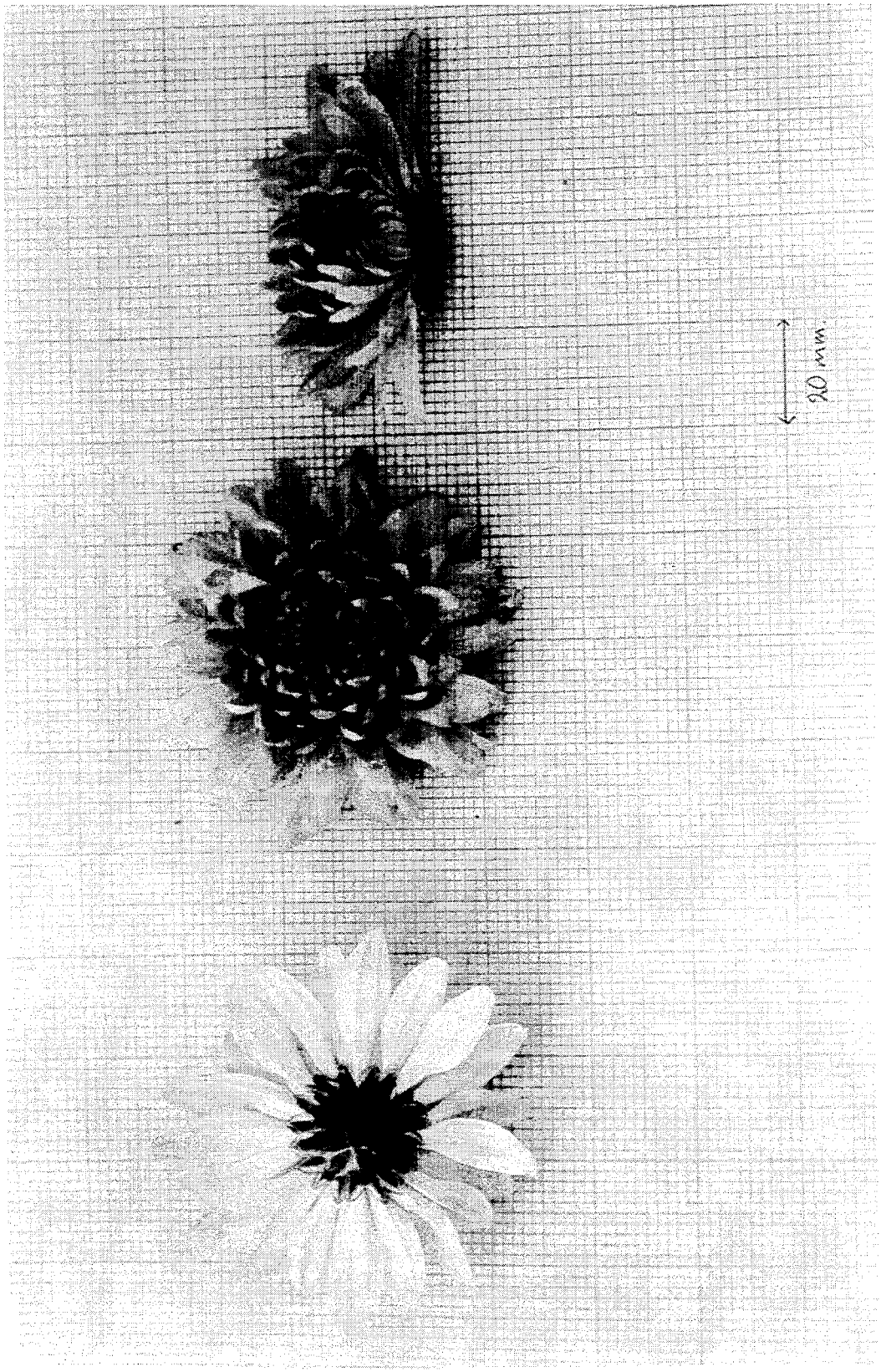
90 mm